United States Patent
Nauha et al.

(10) Patent No.: US 12,195,414 B2
(45) Date of Patent: Jan. 14, 2025

(54) PRODUCTION OF VINYL CHLORIDE MONOMER

(71) Applicant: Coolbrook Oy, Helsinki (FI)

(72) Inventors: Elina Nauha, Helsinki (FI); Tuomas Ouni, Helsinki (FI)

(73) Assignee: COOLBROOK OY, Helsinki (FI)

( * ) Notice: Subject to any disclaimer, the term of this patent is extended or adjusted under 35 U.S.C. 154(b) by 0 days.

(21) Appl. No.: 18/322,014

(22) Filed: May 23, 2023

(65) Prior Publication Data

US 2023/0391695 A1 Dec. 7, 2023

(30) Foreign Application Priority Data

May 20, 2022 (FI) ...................................... 20225449

(51) Int. Cl.
C07C 17/25 (2006.01)
(52) U.S. Cl.
CPC .................... *C07C 17/25* (2013.01)
(58) Field of Classification Search
CPC ........ C07C 17/25; C07C 21/06; B01J 19/002; B01J 19/1806
See application file for complete search history.

(56) References Cited

U.S. PATENT DOCUMENTS

| | | | |
|---|---|---|---|
| 5,488,190 | A | 1/1996 | Le Blevec et al. |
| 7,767,869 | B2 | 8/2010 | Kammerhofer et al. |
| 2020/0114332 | A1 | 4/2020 | Xu et al. |

FOREIGN PATENT DOCUMENTS

| | | | |
|---|---|---|---|
| EP | 3164207 B1 | 12/2018 | |
| EP | 3725403 A1 * | 10/2020 | ............ B01J 19/127 |
| FI | 20206172 A1 | 11/2020 | |

OTHER PUBLICATIONS

Li, Chaochun, et al., "Comprehensive Simulation and Optimization of an Ethylene Dichloride Cracker Based on the On-Dimensional Lobo-Evans Method and Computational Fluid Dynamics", I&EC Research, ACS Publications, dx.doi.org/10.1021/ie302436r | Ind Eng. Chem. Res. 2013, 52, 645-657 (13 pp.).
International Search Report and Written Opinion, PCT/FI2023/050282, dated May 19, 2023 (7 pp.).
Finnish Search Report, dated Nov. 25, 2022 (2 pp.).
Amghizar, Ismael, et al., "Sustainable innovations in steam cracking: CO2 neutral olefin production", Royal Society of Chemistry, React Chem Eng. 2020, 5, 239-257 (19 pp.).
Rubini, Dylan, et al., "A New Turbomachine for Clean and Sustainable Hydrocarbon Cracking", Journal of Engineering for Gas Turbines and Power, Feb. 2022, vol. 144 / 021024-1 (11 pp.).

* cited by examiner

*Primary Examiner* — Jafar F Parsa
(74) *Attorney, Agent, or Firm* — Eversheds Sutherland (US) LLP

(57) ABSTRACT

A method is provided for manufacturing vinyl chloride monomer (VCM), the method comprises subjecting ethylene dichloride (EDC) to thermal cracking to yield a VCM-containing gaseous product, in which method an amount of thermal energy required to heat a stream of EDC-containing process fluid to temperature(s), at which cracking reactions occur, is produced and transferred to said EDC-containing process fluid using a rotary apparatus (100). A VCM production unit and use of the rotary apparatus in production of vinyl chloride monomer from EDC through thermal cracking, are further provided.

19 Claims, 10 Drawing Sheets

PRODUCTION OF VINYL CHLORIDE MONOMER

CROSS-REFERENCE TO RELATED APPLICATION

This application claims priority to Finnish Patent Application No. 20225449, filed May 20, 2022, which is incorporated herein by reference.

FIELD OF THE INVENTION

The present invention generally relates to manufacturing of vinyl chloride monomer from ethylene dichloride. In particular, the invention relates to thermal cracking of ethylene dichloride into vinyl chloride monomer using a rotary apparatus.

BACKGROUND

Vinyl chloride monomer (VCM) or chloroethene is one of the most important bulk chemicals. The main use of VCM is in polyvinyl chloride (PVC) manufacturing, where VCM is used as a monomer building block for the PVC polymer. PVC is currently the second most abundant polymer in the world, behind only polyethylene, with annual production of PVC being globally around 60 million tons. Approximately 96% of VCM is used for the production of PVC.

In the early 20th century, VCM was produced mainly from acetylene, which could be catalytically reacted with hydrochloric acid to yield VCM (rf. equation 1).

$$C_2H_2 + HCl \rightarrow CH_2=CHCl \quad (1)$$

Due to high energy requirements of acetylene production and the hazards associated with acetylene handling, a less energy intensive ethylene dichloride pathway was developed in a mid-20$^{th}$ century. Thereafter, ethylene-based routes have since become predominant. Today, the process of hydrochlorination of acetylene (eq. 1) is obsolete elsewhere except China, where availability of relatively cheap coal maintains this technology at an economically attractive level.

Ethylene-based VCM production is a balanced process, meaning that all intermediates and byproducts are recycled in a way that ensures a closure of the material balance to only VCM as a final product, starting from ethylene, chlorine and oxygen. Ethylene-based pathway proceeds through high-temperature chlorination of ethylene to yield 1,2-ethylene dichloride (EDC; 1,2-dichloroethane) (rf. equation 2.1) followed with thermal decomposition of EDC to yield VCM and hydrochloric acid (rf. equation 2.2).

$$C_2H_4 + Cl_2 \rightarrow C_1CH_2-CH_2Cl \quad (2.1)$$

$$C_1CH_2-CH_2C_1 \rightarrow CH_2=CHCl + HCl (\Delta H=71 \text{ kJ/mol}) \quad (2.2)$$

Thermal decomposition of EDC is carried out through thermal cracking, which may be implemented in liquid- or gas phase. However, the liquid-phase based process is industrially unimportant because expensive chlorine is lost as a salt when EDC is treated with an alkaline solution. Disposal of an aqueous process stream is also associated with several environmental problems. Hence, the gas-phase route carried out via thermal cracking or pyrolysis is the most industrially relevant for the production of VCM.

Gas-phase thermal cracking (pyrolysis) of EDC to VCM consists of a complex set of Cl-catalyzed radical and molecular reactions. While Equation 2.2 present a molecular reaction (an overall reaction), it does not encompass all chemical processes occurring during thermal decomposition of EDC to a VCM-containing product.

Conventional pyrolysis furnace 200 for EDC cracking is illustrated in FIG. 2A. Gas-phase pyrolysis is highly endothermic; therefore, it is typically carried out in tubular coils made of Cr/Ni alloy, placed in a firebox (radiant section) of the furnace. Depending on the design, 16 to 128 coils can be provided in the firebox. The furnace is typically lined with refractory materials. EDC stream passes through radiant coil tubes, where the reactions producing VCM, hydrogen chloride (HCl) and by-products, such as for example acetylene, occur. The effluent gas has its temperature rapidly reduced (product gas quench) to avoid further decomposition of VCM and to minimize formation of byproducts and well as coke and heavy tars. In most processes, cracked gas is cooled down in a quench tower, where condensed and cooled EDC is recirculated at high rates. In some instances, quenching is performed in two stages, first by indirect cooling in transfer line heat exchanger(s) followed with direct quenching. This enables heat recovery for use in other process stages.

Heat required for the endothermic set of pyrolysis reactions is supplied by combustion of fuel in firebox burners. The furnace may be equipped with a single or multiple burners. In most cases, the burner(s) is/are fueled with natural gas. Heat carried out by flue gas is recovered in a convection section of the furnace typically located above the firebox and consisting of a series of tube banks. Heat recovered in the convection section can be used for preheating (evaporating) the hydrocarbon feed (at ca. 200° C.) and dilution media, for example.

Conventional pyrolysis furnace adopted for thermal cracking of ethylene dichloride operates at 50-60% EDC conversion, with gas residence time of about 10 to 30 seconds, pressures of 6 to 35 atm (0.6-3.5 MPa) and gas temperatures between 480-550° C., in some instance, between 500-530° C. Higher temperatures increase the EDC conversion but cause selectivity drop. Operating conditions are typically selected based on a compromise between for example the costs for utilities, production rates and the frequency of shutdown periods.

Although it may be possible to achieve selectivity for the VCM product of up to 99%, in practice, EDC conversion rate still remains moderate. This is because foulants and by-products are formed in the pyrolysis process, causing severe inefficiencies due to large material throughput. For example, coke formation is inevitable in pyrolysis and requires periodic shutdowns of the entire plant for its removal. Other gas phase byproducts, such as chloroprene ($C_4H_5Cl$) and butadiene ($C_4H_6$), also cause difficulties in downstream distillation columns. Conversion rate may be increased slightly by adding a small amount (about 1200 ppm) of carbon tetrachloride ($CCl_4$), an oxychlorination by-product, to enter with the EDC feed. Carbon tetrachloride increases free chlorine radical formation, and it can be used to increase conversion rate to about 60%. However, the chlorine radical also acts as a promoter for undesirable coke formation.

Although several designs are available today for fired furnaces, most vinyl chloride producers have developed their proprietary furnace technology for optimal yield and low shutdown frequency for pipe decoking. Nevertheless, tubular pyrolysis furnaces remain rather large-sized, complex facilities with high greenhouse gas emission burden.

In this regard, an update in the field of vinyl chloride (monomer) manufacture technology is still desired, in view of addressing challenges associated with improving feed-to-product conversion ratios and depleting greenhouse gas emissions in efficient and environmentally friendly manner.

SUMMARY OF THE INVENTION

An objective of the present invention is to solve or to at least mitigate each of the problems arising from the limitations and disadvantages of the related art. The objective is achieved by various embodiments of a method for manufacturing vinyl chloride monomer (VCM), related production unit and uses. In an aspect, a method for manufacturing vinyl chloride monomer (VCM) is provided, according to what is defined in the independent claim 1.

In embodiment, the method comprises: subjecting ethylene dichloride (EDC) to thermal cracking to yield a VCM-containing gaseous product, wherein an amount of thermal energy required to heat a stream of EDC-containing process fluid to temperature(s), at which cracking reactions occur, is produced and transferred to said EDC-containing process fluid using a rotary apparatus comprising: a rotor with a plurality of rotor blades arranged into at least one row over a circumference of a rotor hub mounted onto a rotor shaft; a plurality of stationary guide vanes arranged into row(s) upstream of the rotor blades; and a stationary diffuser arranged downstream of the rotor blades, wherein the rotor, the stationary guide vanes and the diffuser are enclosed in a duct formed in the rotary apparatus between at least one inlet and at least one outlet, and wherein the amount of thermal energy is produced, in the rotary apparatus, by virtue of series of energy transformations occurring when a stream of fluidic medium propagated in the duct between the inlet(s) and outlet(s) successively passes through the stationary guide vanes, the rotor blades and the diffuser, respectively.

In embodiment, the method comprises subjecting EDC to thermal cracking in the rotary apparatus, wherein cracking reactions are initiated in the EDC-containing process fluid propagating through the rotary apparatus by virtue of adding the amount of thermal energy required for the cracking reactions to occur directly to the stream of EDC-containing process fluid.

In embodiment, the method comprises subjecting EDC to thermal cracking in a pyrolysis furnace suitable for that purpose, the method further comprises:
  in the rotary apparatus, generating a heated fluidic medium by virtue of adding the amount of thermal energy to the fluidic medium propagating therethrough, and
  using said fluidic medium as a carrier to transfer thermal energy to the pyrolysis furnace and to heat the stream of EDC-containing process fluid, flowing through said pyrolysis furnace, to the temperature(s), at which cracking reactions occur.

In embodiment, the heated fluidic medium used as the thermal energy carrier is any one of air, nitrogen gas, steam, flue gas(-es) exhausted from the pyrolysis furnace, and any combination thereof. The pyrolysis furnace can be any cracking furnace suitable for thermal cracking of ethylene dichloride containing feed.

In embodiment, the method comprises connecting at least two rotary apparatuses into a system, in which a first apparatus is rendered with a preheater function to (pre)heat the EDC-containing process fluid, and a second apparatus arranged downstream of the first apparatus is rendered with a thermal cracker function.

In embodiment, the method further comprises conducting an amount of input energy into the at least one rotary apparatus, wherein, by adjusting the amount of said input energy conducted into the at least one rotary apparatus, the amount of thermal energy added to the stream of fluidic medium propagated through the rotary apparatus is regulated. In embodiment, the input energy is electrical energy.

In embodiment, the amount of electrical energy conducted as the input energy into the at least one rotary apparatus is within a range of about 5 percent to 100 percent.

In embodiment, the amount of electrical energy conducted as the input energy into the at least one rotary apparatus is obtainable from a source of renewable energy or a combination of different sources of energy, optionally, renewable energy.

In embodiment, the method comprises adjusting velocity and/or pressure of the stream of fluidic medium propagating through the rotary apparatus to produce conditions, at which an amount of kinetic energy added to the stream of fluidic medium by rotating blades of the rotor is sufficient to raise the temperature of the fluidic medium to a predetermined value when said stream of fluidic medium exits the at least one row of rotor blades at a supersonic speed and passes through the stationary diffuser, where stream decelerates and dissipates kinetic energy into an internal energy of the fluidic medium, whereupon the amount of thermal energy is added to the stream of fluidic medium.

In embodiment, in said method, the amount of thermal energy added to the stream of fluidic medium propagating through the apparatus is produced by virtue of generation of a system of shock waves during successive propagation of said stream of fluidic medium through the rows of stationary guide vanes, the row of rotor blades and the stationary diffuser, respectively, in a controlled manner.

In an aspect, a method for manufacturing polyvinylchloride (PVC) is provided, according to what is defined in the independent claim 13. The method comprises manufacturing pf PVC through polymerization of a VCM product obtained by a method according to the previous aspect.

In an aspect, a vinyl chloride monomer (VCM) production unit for manufacturing VCM from ethylene dichloride (EDC) through thermal cracking is provided.

In an aspect, a method of use of the rotary apparatus in production of vinyl chloride monomer (VCM) from ethylene dichloride (EDC) through thermal cracking is provided, according to what is defined in the independent claim 15.

The utility of the present invention arises from a variety of reasons depending on each particular embodiment thereof.

On the whole, the invention aims at improving a conventional EDC cracking process by integrating into said process a rotary apparatus described herein below. The following issues pertinent to the existing EDC cracking technology can be improved:
  Selectivity of a main reaction (VCM production) is improved by suppressing byproduct formation.
  Once-through yields significantly exceeding the same of conventional EDC furnaces are achieved.
  Equipment used for EDC cracking can be considerably reduced in size.
  Formation of coke and other foulants is reduced and a run length of the EDC cracking reactor is extended by having coke formation suppressed.
  Energy-efficiency (energy used per mass unit of VCM produced) of the EDC cracking process is markedly improved.

Greenhouse gas emissions, such as carbon dioxide emissions, per mass unit of VCM produced is reduced through electrification of EDC cracking/VCM production.

Overall, the rotary apparatus used in the method presently disclosed allows for inputting heat into the EDC-containing process fluid, directly or indirectly, wherein the amount of heat inputted into the process is sufficient to initiate and maintain, to a predetermined extent, cracking reactions of ethylene dichloride to produce vinyl chloride (monomer).

Direct heating involves propagating of the EDC-containing process fluid through the rotary apparatus. In this manner, heating of the process fluid is achieved extremely fast, since the need to transfer heat from the external heater through the reactor wall is eliminated. This absence of external heating results in lower reactor surface temperatures, which, in turn, leads to much lower coke production during the cracking process. Hence, the cracker can be operated for longer time periods between decoking shutdowns. Moreover, direct heating allows for raising the temperature of the process fluid above that of conventional EDC cracking (500-550° C.). This increases the rate of EDC cracking reactions and hence results in shorter residence time the reactants spend in a process space. As a result, the EDC cracker can be considerably reduced in size. Alternatively, once-through conversion rates can be improved in the equipment of a standard (non-reduced) size.

Indirect heating involves heating, in the rotary apparatus, of fluid(s) other than the EDC-containing feed and further using said fluid(s) as a heat transfer medium to input thermal energy into a EDC pyrolysis furnace. This approach allows for revamping any existing EDC cracker into a low emission, high energy-efficiency furnace. Replacing fired heater(s) by the rotary apparatus(-es) in conventional furnaces does not require major changes in infrastructure and is therefore very cost-effective.

Indirect heating approach is further associated with improved control over cracking temperature. In fired heaters the temperature of the flame is very high, in the range of 1800-2200° C. depending on fuel and (air) pre-heating. These extremely high temperatures will heat the furnace coil tubes accordingly and cause accelerated coking. By applying the rotary apparatus technology, the EDC cracking furnace temperature can be maintained at lower levels and the input heat can be more uniformly distributed across the furnace. This will result in decreased coking tendency and hence increase conversion rates well above typical once-through conversion values of about 60%.

The invention further allows to decrease greenhouse gases ($CO$, $CO_2$, $NOx$, $SOx$) and particle emissions produced in conventional EDC cracking. This can be achieved by electrically driven rotary apparatuses and integrating said rotary apparatuses into conventional EDC cracking plants in closed or semi-closed heating loops; therefore, energy efficiency of the processes is improved by reducing flue gas heat losses. In conventional heaters, flue gases can be recycled only partly.

The expression "a number of" refers hereby to any positive integer starting from one (1), e.g. to one, two, or three. The expression "a plurality of" refers hereby to any positive integer starting from two (2), e.g. to two, three, or four. The terms "first" and "second", are used hereby to merely distinguish an element from another element without indicating any particular order or importance, unless explicitly stated otherwise.

In present disclosure, the terms "thermal cracking" and "pyrolysis" are used interchangeably.

In present disclosure, the term "gasified" is utilized to designate matter being converted into a gaseous form by any possible means.

Different embodiments of the present invention will become apparent by consideration of the detailed description and accompanying drawings.

DETAILED DESCRIPTION OF THE EMBODIMENTS

Detailed embodiments of the present invention are disclosed herein with the reference to accompanying drawings.

FIGS. 1A, 1B, 2B and 3 schematically illustrate basic layouts for a method of manufacturing vinyl chloride monomer (VCM) from ethylene dichloride (EDC) through a process of thermal cracking, according to the embodiments, and the same for a related VCM production unit. The VCM production method and the VCM production unit generally configured to implement said method are thus designated with a common reference number 101.

The VCM production unit can be further integrated into an industrial plant, a factory, or any industrial system (not shown) comprising equipment designed to perform an industrial process or a series of industrial processes aiming at obtaining vinyl chloride (monomer) from ethylene dichloride-containing feed. Mentioned industrial plant may include additional units or facilities for manufacture, extraction and/or refinement of related materials (such as for example feedstocks, intermediates, products and any auxiliary chemicals employed in the process) and/or power. The industrial plant can include for example a facility for chlorination of ethylene to yield 1,2-ethylene dichloride (EDC) and/or a facility for manufacturing polyvinylchloride (PVC) by polymerization of the VCM.

In an aspect, present invention pertains to a method for manufacturing vinyl chloride monomer (VCM) from ethylene dichloride (EDC), by subjecting EDC feed to thermal cracking (pyrolysis) to yield a VCM-containing gaseous product. An amount of thermal energy required to heat a stream of EDC-containing process fluid to temperature(s), at which cracking reactions occur, is produced and transferred to said stream of EDC-containing process fluid using a rotary apparatus 100, 100-1, 100-2.

Figure 4A:
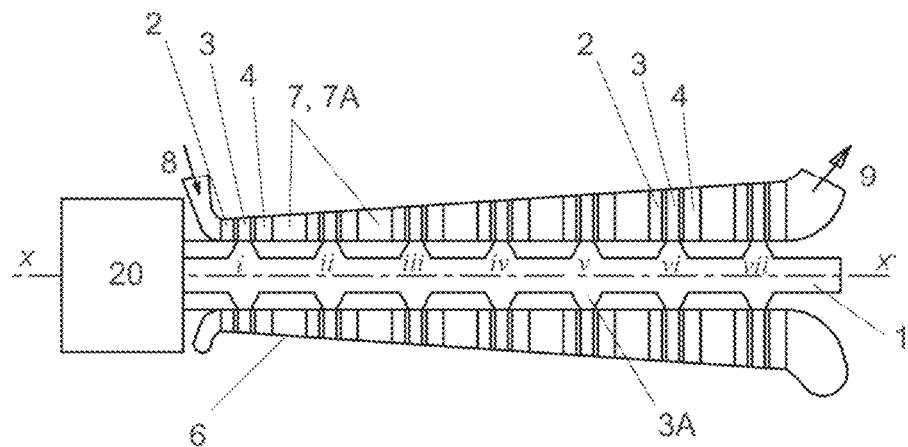
FIGS. 4A-4C are vertical crosscuts of a rotary apparatus 100 (100A, 100B and 100C, respectively) configured to implement the method according to the embodiments.
Figure 4B:
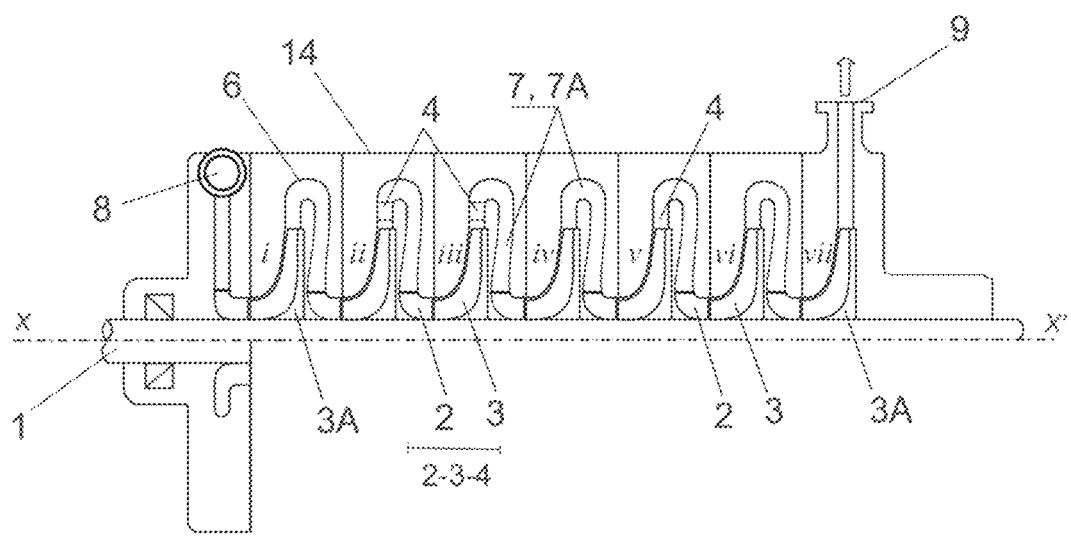
Figure 4C:
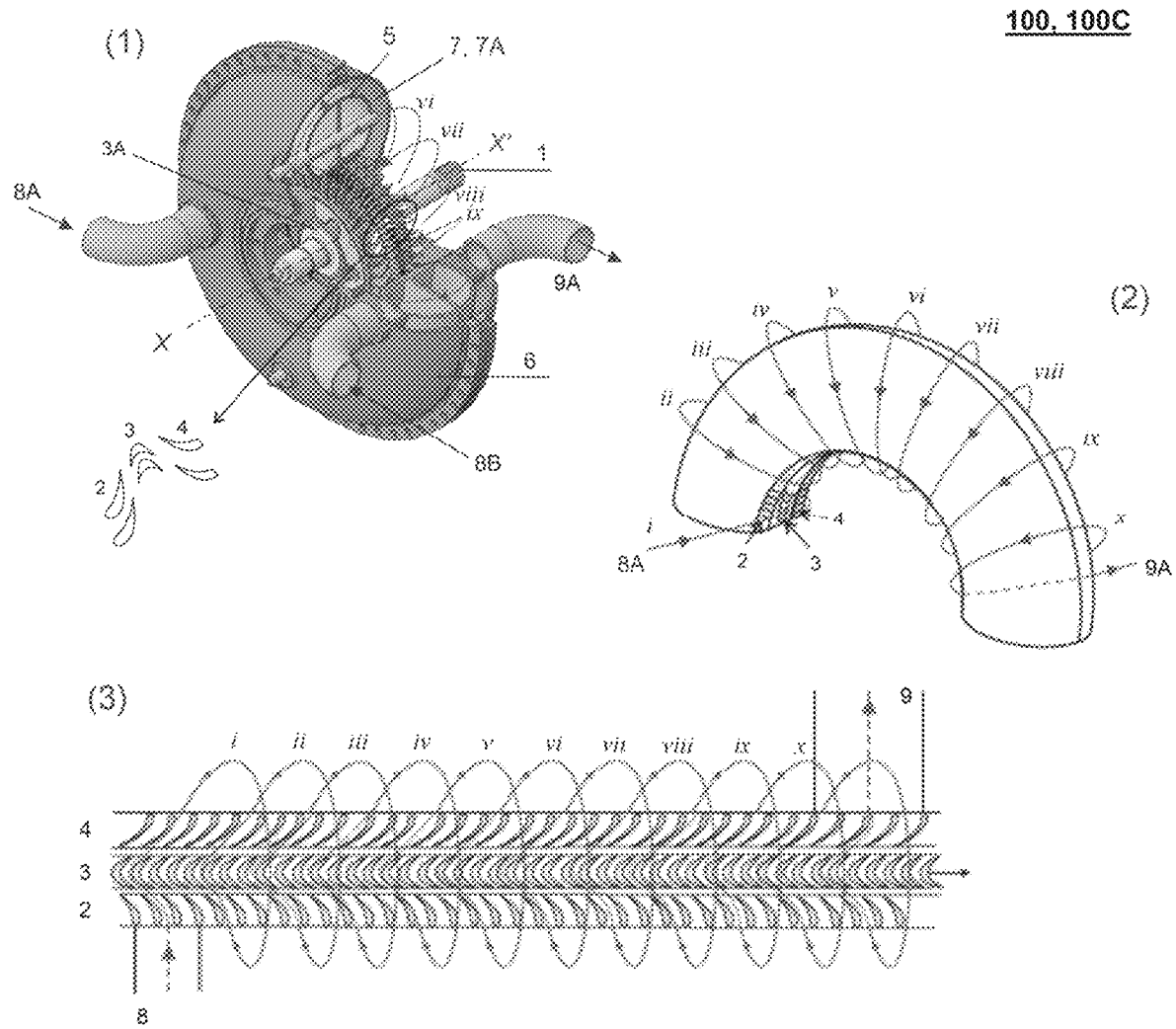

Reference is made to FIGS. 4A, 4B and 4C schematically illustrating different implementations (100A, 100B and 100C, respectively) of the rotary apparatus 100. It is further assumed that based on the following description, a skilled person would be capable to practise the invention using different configurations of the rotary apparatus including those not explicitly disclosed herewith.

The rotary apparatus 100, configured to heat the stream of EDC-containing process fluid, directly or indirectly, comprises: a rotor with a plurality of rotor blades arranged into at least one row over a circumference of a rotor hub mounted onto a rotor shaft; a plurality of stationary guide vanes arranged into row(s) upstream of the rotor blades; and a stationary diffuser arranged downstream of the rotor blades. Rotor and stationary components are enclosed in a duct formed in the rotary apparatus between at least one inlet and at least one outlet. The amount of thermal energy required to heat the stream of EDC-containing process fluid, directly or indirectly, to temperature(s), at which cracking reactions occur, is produced in the rotary apparatus by virtue of series of energy transformations occurring when a stream of fluidic medium propagated in the duct between the inlet(s) and outlet(s) successively passes through the stationary guide vanes, the rotor blades and the stationary diffuser, respectively.

In the VCM production unit, the apparatus 100 (100A, 100B and 100C) can be provided as a standalone or as a number of apparatuses arranged in series (in sequence) and/or parallel (in arrays). The apparatus 100 operates under a concept that it is capable to transfer the mechanical energy of rotating shaft to fluidic media and to convert it into internal energy of the fluid through a set of stationary and rotating components within a number of working stages. When fluidic flow dissipates its kinetic energy into internal energy of the fluid, it provides the amount of thermal energy (heat) to the fluidic stream, thus increasing the fluid temperature. Aerodynamic design of the apparatus 100 can vary.

FIG. 4A illustrates an axial-type apparatus 100, 100A, in which rotating and stationary vanes are encompassed in an essentially tubular casing, as described in the U.S. Pat. No. 9,234,140 to Seppala et al. FIG. 4B illustrates a configuration 100, 100B outlined in the U.S. Pat. No. 10,744,480 to Xu & Rosic. In configuration 100, 100C shown on FIG. 4C, the process fluid propagates between the inlet and the outlet along a flow path established in accordance with essentially helical trajectory formed within an essentially toroid-shaped casing, wherein fluidic flow successively passes through the rows of stationary guide vanes, rotor blades and stationary diffuser vanes. Devices of the kind are discussed in detail in U.S. Pat. No. 9,494,038 to Bushuev and U.S. Pat. No. 9,234,140 to Seppala et al. Alternatively, the method according to the embodiments can be further realized using a rotary apparatus configured to implement the fluidic flow along the flow path established by virtue of the stream of fluidic medium in the form of two spirals rolled up into vortex rings of right and left directions, as outlined in the U.S. Pat. No. 7,232,937 to Bushuev (not shown). The above mentioned documents are considered incorporated herein by reference.

In all configurations, 100A, 100B and 100C, the apparatus 100 comprises a rotor system, hereafter, a rotor, comprising a rotor shaft 1 positioned along a horizontal (longitudinal) axis X-X' and a plurality of rotor blades (also referred to as working blades) arranged into at least one row over a circumference of a rotor hub or a rotor disk 3A mounted onto the rotor shaft. The plurality of rotor blades arranged into the (blade) row establish a rotor blade assembly or a rotor blade cascade 3.

The rotary apparatus further comprises a drive system, including at least one motor and an associated drive, to drive the rotor. Drive system is designated with a reference numeral 20 on FIG. 4A. In embodiments, the motor is an electric motor (i.e. a device capable of transferring energy from an electrical source to a mechanical load). Additionally or alternatively, the rotary apparatus can be directly driven by gas- or steam turbine, for example, or any other appropriate drive device.

The apparatus 100 further comprises a stationary (stator) component, formed with a number of structures defining a reaction space (e.g. a casing 6), and a plurality of stationary vanes arranged into at least one row adjacent to a corresponding row of rotor blades. The apparatus further comprises a stationary diffuser, which can be vaned or vaneless.

In some configurations, the apparatus comprises a plurality of stationary guide vanes 2 arranged into at least one row upstream of a corresponding row of rotor blades. Stationary guide vanes can be configured as stationary nozzle guide vanes (NGV). In some configurations, the apparatus additionally comprises a plurality of stationary diffuser vanes 4 arranged into at least one row downstream of a corresponding row of rotor blades. The rows of stationary vanes form stationary guide vane cascade(s) 2 and stationary diffuser vane cascade(s) 4, respectively.

The term "cascade" (a crown of blades) refers to an ensemble of (working) blades installed over a periphery of a rotor disk/rotor hub or (stationary) blades installed directly or indirectly on an internal wall of the casing. For clarity, stationary blades are referred to in the present disclosure as "vanes".

The terms "upstream" and "downstream" refer to spatial and/or functional arrangement of structural parts or components with relation to a predetermined part- or component, hereby, the at least one rotor blade row, essentially in a direction of fluidic flow throughout the apparatus (along the axis X-X', rf. FIGS. 4A-4C).

In some configurations, provision of the diffuser vane cascade 4 may be omitted.

The apparatus comprises the gas-tight casing 6 (also referred to as a gas casing or a pressure casing), in where an internal passageway 7 is established in the form of a duct or a conduit spread between at least one inlet 8 and at least one outlet 9. Inner surface of the casing 6 faces the duct 7. In some configurations, the duct 7 is defined with the inner surface of the casing. Shape of the conduit/duct 7 varies depending on the apparatus configuration.

In present disclosure, the gas casing 6 is generally referred to as an apparatus casing. In practice, the apparatus 100 can be further enclosed into a separate external housing (rf. external housing 14 shown on FIG. 4C).

The duct 7 formed in the casing is configured to substantially fully enclose the periphery of the rotor with a plurality of working blades assembled thereon, the stationary guide vanes and the diffuser.

In the apparatus 100, arrangement of stationary and working components, such as blade rows 2, 3, and 4, in the internal passageway (duct 7) within the casing is such that a vaneless portion or portions 7A (a so-called vaneless space) is created between an exit from the diffuser 4 disposed downstream of the rotor blades and configured, in some instances, as a row of stationary diffuser vanes, and an entrance to the row of stationary guide blades 2 disposed upstream of the rotor blades.

The apparatus 100 is configured with a number of elemental stages also referred to as working (process) stages. Each working stage is formed with a successive arrangement of a row of stationary guide vanes 2 ("stator"), a row of rotor blades 3 ("rotor") and a diffuser 4 ("diffuser"), which together form a stator-rotor-diffuser stage sequence. The "diffuser" component in the sequence can be formed with a row of diffuser vanes, a vaneless diffuser or a part of a vaneless space arranged after the rotor blades. A single stage- or multistage configurations including 2-30 rows of rotor blades mounted on the rotor shaft can be conceived. Some exemplary multistage configurations include 10 to 20 rotor blade rows. In multistage configurations, the stages can be driven by the same or different (e.g. joined) rotor shafts.

On FIGS. 4A-4C, working stages are designated with roman numerals (i-x; i-vii). Total number of stages is determined by the process duty, required temperature and/or pressure level, and other process related parameters.

Function of the elemental stage is to mediate an energy conversion cycle, during which mechanical energy of the rotor shaft is converted into kinetic energy—and further—into internal energy of the fluid, followed by the rise of fluid temperature. That is, while the rotor is configured to impart mechanical energy to the process fluid, the vaned or vaneless diffuser located downstream of the rotor is further configured to convert mechanical (kinetic) energy of the process fluid into internal energy of said process fluid. In the diffuser area, the high speed fluid flow arriving from the rotor is diffused with the significant entropy increase, whereby the flow dissipates kinetic energy into the internal energy of the fluidic substance, thus providing thermal energy into the fluid.

During the energy conversion cycle, the stationary guide blade row(s) 2 disposed upstream the rotor blades 3 prepare required flow conditions at the entrance of the rotating blade row (cascade). In the rotor blade row, mechanical energy of the shaft and rotating blades is transferred to fluidic stream. In at least the part of each rotor blade row 3 the fluid stream can reach a supersonic flow condition.

The diffuser 4 disposed downstream the rotor blades 3 convert(s) mechanical energy of the fluid into its thermal energy (heat). Stream of fluidic medium exits the rotor blades 3 and enters the diffuser at supersonic speed. If the flow upstream of the diffuser is supersonic, the kinetic energy of the fluidic stream is converted into internal energy of the fluid through a system of multiple shocks and viscous mixing and dissipation. The flow dissipates its kinetic energy into internal energy of the fluidic stream propagating through the reactor (along the duct 7) and thus adds the amount of thermal energy to the fluid. An increase in the internal energy of the fluid results in a rise of fluid temperature.

In configuration 100A shown on FIG. 4A, the apparatus is generally configured as an essentially tubular, axial-type turbomachine. The apparatus 100A comprises an elongated rotor 1 which extends along the horizontal axis X-X'. A plurality of rotor blades is arranged along a rotor hub 3A into a number of sequential rows to form rotor blade cascade(s) 3. The rotor 1 is enclosed within the casing 6, inner surface of which is provided with the first- and second stationary vane cascades 2 and 4, respectively, arranged such that blades/vanes of rotor- and stator cascades 2, 3 and 4 alternate along the rotor 1 in the longitudinal direction (along the axis X-X'). Rows of stationary vanes 2, 4 can be arranged on opposite sides of the casing (inner) surface facing the duct. Working stages i-vii are established, wherein each stage is formed with a rotor blade cascade 3 and adjacent pairs of stator vanes 2, 4. A portion 7A of the duct free of blades/vanes is arranged between subsequent stages.

The casing 6 may be a cone-shaped or it may have an essentially constant cross-section along its entire length (not shown).

In configuration 100B shown on FIG. 4B, the apparatus 100 is configured as a radial turbomachine that generally follows a design for centrifugal compressors or centrifugal pumps. The term "centrifugal" implies that fluid flow within the device is radial; therefore, the apparatus 100B is referred to as a "radial-flow apparatus". The apparatus embodied at 100B comprises a number of working stages (i-vii), wherein each stage may be represented with the stationary guide vane cascade 2, the rotor blade cascade 3 and the diffuser 4. The diffuser is installed in an essentially U-shaped conduit provided as a part of a duct 7 followed with a vaneless portion 7A. The diffuser may be formed with or without diffuser vanes. In some configurations, a vaneless U-shaped conduit located downstream the rotor blade cascade may be adopted, by virtue of its three-dimensional shape, to form a diffuser area (rf. stage v), in which mechanical energy imparted to the process fluid by the rotor is converted into heat. Provision of vaned diffuser 4 is shown, on FIG. 4B, for stages ii and iii; however, the rows of diffuser vanes, for example, may be installed downstream of each rotor blade cascade 3 (stages i-vii).

In addition to multistage configurations 100A, 100B comprising a number of working stages successively arranged along the rotor shaft, the apparatus 100 may comprise a number of stages arranged into a regenerative multistage configuration, as illustrated in FIG. 4C.

FIG. 4C, shows, at illustration (1), the apparatus 100C configuration with two inlets 8 (8A, 8B) and two outlets 9 (9A, second outlet is not shown); other configurations may be conceived, where appropriate.

The apparatus 100 embodied as 100C, is rendered with an essentially toroid shape (a "doughnut" shape) of the casing 6 in three-dimensional configuration, whereby the rotor system (1, 3A, 3) with related bearing assemblies (not shown) may be viewed as filling up an aperture defining an opening in the central part of the toroid. At its meridional cross-section, the casing 6 is essentially ring-shaped.

In the apparatus 100C, stationary vane cascades 2, 4 are provided as essentially annular assemblies at both sides of the rotor blade cascade 3.

The apparatus in configuration 100C further comprises a flow-shaping device (a flow-guiding device) 5 arranged inside the gas casing and configured as an internal stationary ring-shaped structure, which accounts for establishing an essentially annular duct inside the casing 6. The flow-shaping device 5 may be provided as an annular, essentially hollow structure, such as a hoop, for example.

In configuration 100C, the internal passageway is defined with a volume created between the gas casing 6 (an outer "doughnut") and the internal flow-shaping device 5 (an inner "doughnut"). This internal passageway (the duct 7) formed between an inner surface of the gas casing 6 and an outer surface of the flow-shaping device 5 thus adopts an essentially annular shape with essentially ring-shaped meridional cross-section.

In the casing 6, the blade rows 2, 3, 4 adjoin each other in such a way that the vaneless portion 7A of the duct 7 situates between the exit from the stationary diffuser blade row 4 and the entrance into the stationary guide vane row 2.

The working stage is established with the three rows of blades (2, 3, 4), as described herein above. In configuration 100C, the flow exiting from the exit of the diffuser blade row 4 of one stage (stage i, for example) follows a helical (helico-toroidal) path in the duct 7/vaneless portion 7A thereof and enters the row of stationary guide vanes 2 of the next stage (stage ii). The flow passes through the successive blade rows 2, 3, 4 (stage ii), exits the diffuser 4 (stage ii), and continues towards next stage(s) iii-x until the flow reaches the outlet the outlet 9, 9A (rf. illustrations (2) and (3); where illustration 3 shows all stages i-x plotted on the same plane). Direction of the flow is indicated with an arrow.

In the VCM production unit, at least two rotary apparatuses may be connected in parallel and/or in series. Connection between the rotary apparatuses 100 can be mechanical and/or functional. Functional connection (such as connection realized in terms of achievable heat input, for example) can be established upon association between at least two individual, physically integrated- or non-integrated individual apparatus units. In a latter case, association between the at least two rotary apparatuses can be established via a number of auxiliary installations (not shown). In some configurations, at least two rotary apparatuses can be at least functionally connected via their rotor shafts such, as to mirror each other. Rotary apparatuses connected into arrays and/or sequences, may have different type of drive engine, e.g. the electric motor driven reactor(s) can be combined with those driven by steam turbine, gas turbine and/or gas engine.

The method disclosed hereby further comprises conducting an amount of input energy into the at least one rotary apparatus 100. In embodiments, the input energy comprises electrical energy. In present disclosure the amount of electrical input energy is defined in terms of electric power, i.e. as a rate of energy transfer per unit time (measured in Watt). By adjusting the amount of said input energy, such as electrical energy, conducted into the at least one rotary apparatus, the amount of thermal energy added to the stream of fluidic medium propagated through the rotary apparatus can be regulated.

The amount of electrical energy conducted as the input energy into the at least one rotary apparatus is provided within a range of about 5 percent to about 100 percent. In some instances, the amount of electrical energy used as the input energy is within a range of about 50 to about 100 percent. The amount of electrical energy can constitute any one of: 5, 10, 15, 20, 25, 30, 35, 40, 45, 50, 55, 60, 65, 70, 75, 80, 85, 90, 95, and 100 percent (from the total energy input), or any intermediate value falling in between the above indicated points.

Electric power (defined as the rate of energy transfer per unit time) can be supplied into the rotary apparatus through supplying electric current to the electric motor used to propel a rotary shaft of the apparatus. Supply of electric power into the rotary apparatus can be implemented from an external source or sources (as related to the rotary apparatus 100 and/or the VCM production unit). Additionally or alternatively, electrical energy can be produced internally, within the VCM production unit and/or within a related industrial system (e.g. plant or factory) incorporating said unit.

External source or sources include a variety of supporting facilities rendered for sustainable energy production. Thus, electric power can be supplied from an electricity generating system that exploits at least one source of renewable energy or a combination of the electricity generating systems exploiting different sources of renewable energy. External sources of renewable energy can be provided as solar, wind- and/or hydropower. Thus, electric power may be received into the process from at least one of the following units: a photovoltaic electricity generating system, a wind-powered electricity generating system, and a hydroelectric power system. In some exemplary instances, a nuclear power plant may be provided as the external source of electrical power. Nuclear power plants are generally regarded as emission-free. The term "nuclear power plant" should be interpreted as using traditional nuclear power and, additionally or alternatively, fusion power.

Electricity can be supplied from a power plant that utilizes a turbine as a kinetic energy source to drive electricity generators. In some instances, electric power to drive the at least one apparatus 100 can be supplied from at least one gas turbine (GT) provided as a separate installation or within a cogeneration facility and/or a combined cycle power facility, for example. Electric power can thus be supplied from at least one of the following units: a combined cycle power facility, such as a combined cycle gas turbine plant (CCGT), and/or a cogeneration facility configured for electricity production combined with heat recovery and utilization through combined heat and power (CHP), for example. In some examples, the CHP plant can be a biomass fired plant to increase the share of renewable energy in the process described. Additionally or alternatively, supply of electric power can be realized from a spark ignition engine, such as a gas engine, for example, and/or a compression engine, such as a diesel engine, for example, optionally provided as a part of an engine power plant. Still further, any conventional power plant configured to produce electrical energy from fossil raw materials, such as coal, oil, natural gas, gasoline, and the like, typically mediated with the use of steam turbines, can be used to generate electrical energy as an input energy for the rotary apparatus 100. Hydrogen can also be utilized as a source of renewable energy, to be reconverted into electricity, for example, using fuel cells.

Any combination of the abovementioned sources of electric power, realized as external and internal sources, may be conceived.

Conducting input energy, comprising electrical power, into the drive system of the rotary apparatus can be further accompanied with conducting mechanical shaft power thereto from a power turbine, for example, optionally utilizing thermal energy generated elsewhere. Shaft power is defined as mechanical power transmitted from one rotating element to another and calculated as a sum of the torque and the speed of rotation of the shaft. Mechanical power is defined, in turn, as an amount of work or energy per unit time (measured in Watt).

In practice, the shaft power from the electric motor and the power turbine, for example, can be divided so that any one of those can provide the full shaft power or a fraction of it.

Figure 1A:
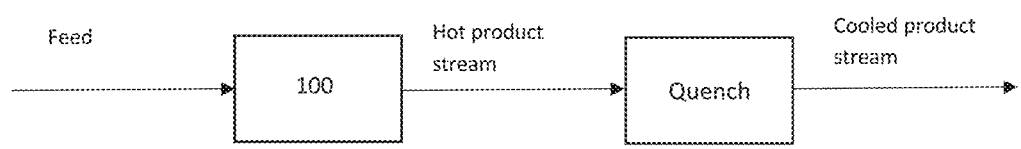
FIGS. 1A and 1B are schematic representations of a VCM production method and related production unit according to the embodiments.
Figure 1B:
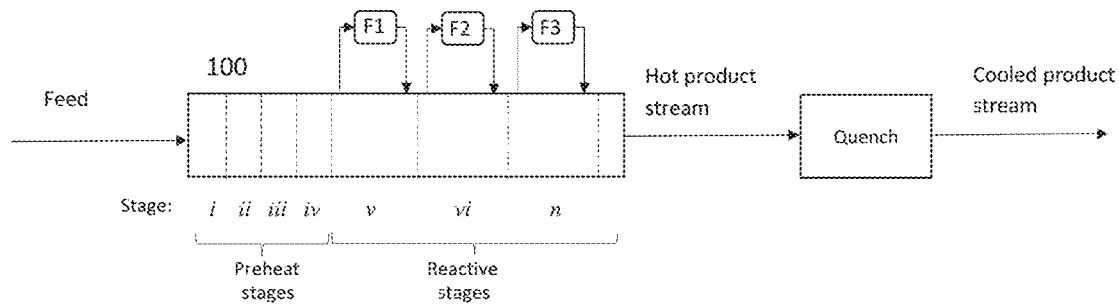

Reference is made back to FIGS. 1A and 1B illustrating embodiments which involve using the rotary apparatus 100 in direct heating of the process fluid.

The method comprises subjecting EDC-containing feed to thermal cracking directly in the rotary apparatus 100 (100A, 100B, 100C). EDC-containing feed enters the apparatus 100 via the inlet(s) 8, 8A, 8B (rf. FIGS. 4A-4C), and a stream of the EDC-containing process fluid flows along the duct 7 towards outlet(s) 9, 9A, 9B following a flowpath specific for each type of the apparatus. The amount of thermal energy required to heat a stream of EDC-containing process fluid to temperature(s), at which cracking reactions occur, is thus transferred, hereby, added, directly to the EDC-containing process fluid flowing through the apparatus.

The amount of thermal energy required to heat the stream of EDC-containing process fluid to temperature(s), at which cracking reactions occur, is produced in the rotary apparatus by virtue of series of energy transformations occurring when a stream of fluidic medium propagated in the duct between the inlet(s) and outlet(s) successively passes through the stationary guide vanes, the rotor blades and the stationary diffuser, respectively.

In configurations outlined on FIGS. 1A and 1B, the rotary apparatus 100 acts as a cracking reactor (a cracking furnace).

Fluidic flow propagating through the apparatus 100 sequentially passes through several working stages, and with each passage the temperature of the process fluid is raised by a certain value. More precisely, temperature rise occurs when the stream of process fluid exits the rotor blades and passes through the diffuser and the vaneless space. Increased temperatures promote thermal degradation of feedstock species and conversion thereof into desired products. An amount of thermal energy added to the fluid is sufficient to initiate chemical degradation reactions, in particular reactions resulting in breaking down carbon-hydrogen (C—H) and carbon-chlorine (C—Cl) bonds. Hence, ethylene dichloride molecules present in the fluidic stream decompose to yield vinyl chloride (monomer) having lower molecular weight.

In the approach involving direct heating of reactants in the apparatus 100, the EDC feed along with possible co-reactants, such as chlorine or chlorohydrocarbons, enter, preferably in gaseous form, the apparatus 100. The gaseous feed passes through a series of stator-rotor-diffuser stages, wherein propagation through each such stage results in addition of a portion of thermal energy into the process fluid (gas) as the kinetic energy inputted to the stream by rotation of the rotor shaft/blades dissipates into thermal energy of the fluid via a system of shockwaves. Temperature of the process fluid increases with each subsequent stage. In other words, temperature of the process fluid increases stepwise until the EDC cracking temperature value is achieved, and EDC decomposition starts to occur. As temperature rise continues, the EDC cracking reaction rate increases, and the endothermic reaction starts reducing the temperature of reactants between the stages. The gaseous reactants are passed through a number of stages so that desired conversion of the EDC raw material is achieved. After being discharged from the apparatus 100, a hot product stream is subjected to rapid cooling (quench) to stop the reaction from proceeding further. A cooled product stream is directed from a cooling arrangement (such as a quench tower, transfer line exchanger(s)/TLE(s), and the like) towards a separation section (not shown).

Prior to entering the apparatus 100, the EDC feed can be preheated to a predetermined temperature (inlet temperature).

As heat generation in the apparatus 100 acting as a cracking reactor (cracking furnace) takes place inherently in the process fluid, via a mechanism of shockwave dissipation of kinetic energy into thermal energy, there is no need to transfer heat into the process fluid through the reactor surfaces (viz. through the metal surfaces of tubular coils), as it is typically done in conventional cracking furnaces equipped with fired heaters. Therefore, an extremely fast heating of fluidic medium propagating through the apparatus can be achieved. Residence time the fluid spends to pass through the working stage (a stator-rotor-diffuser sequence) is in scale of fractions of seconds, such as about 0.1-10 milliseconds (0.0001-0.01 seconds). This results in a heating rate that is a few magnitudes faster than in conventional fired heaters, where the heat is transferred through the walls of tube coils via conduction and convection.

Since there is no need to transfer external heat to the reactants, such absence of external heating results in lower reactor surface temperatures (compared to conventional EDC cracker). Due to lower surface temperatures, less coke and other foulants is formed; therefore, operational time periods between decoking shutdowns are extended.

By virtue of above indicated benefits, temperature of the process fluid can be increased above that of the typical EDC cracking procedure (500-550° C.).

Overall, the process flow related parameters, such as flow velocity and temperature, can be adjusted as required. When the apparatus 100 is used as a cracking reactor, temperature rise can be within a range of about 10° C. to about 120° C. in one stage. Hence, the stream of fluidic medium propagating through the apparatus 100 can be heated to about 1000° C. in a "once-through" configuration (taken 100° C. temperature rise per stage in a 10-stage apparatus) in extremely short time periods. This increases the rate of EDC cracking reactions, markedly reduces reaction times and hence allows for achieving same once-through conversion rates in a reactor having significantly smaller size (as compared to a conventional cracking furnace).

Alternatively, adjusting the operating temperature to higher rates (i.e. higher than "conventional" EDC cracking temperatures) allows for increasing the once-through conversion rate in reactors of similar size.

FIG. 1A illustrates, at 101, 101A, a VCM production method and a related production unit adapted for cracking EDC in a single apparatus 100 to yield VCM. Configuration of FIG. 1A is put into practice by optimizing reaction temperatures up to the levels where pyrolysis proceeds at a rate which enables EDC conversion within a single reactor device. The apparatus 100 (FIG. 1A) may be adapted for instant heating of the EDC-containing feed or, alternatively, pyrolysis temperature(s) may be achieved in a number of working stages (as described herein below).

Temperature of fluidic medium, propagating through working stages of the apparatus 100 can be optimized as required. In particular, temperature rise per stage may be optimized such to promote thermal decomposition of EDC in all stages or in selected stages. Configuration, where a number of working stages (i-iv) are designated with a function of (pre)heating the EDC feed to a predetermined temperature is shown in detail on FIG. 1B. FIG. 1B shows a configuration, where after having passed three or four so-called (pre)heating stages, the process stream reaches the temperature at which the feed starts to actively decompose. In practice, decomposition reactions may occur already after the process fluid has passed the first working stage. Working stages within a duct region, where actual cracking reactions occur, are referred to as reactive stages.

FIG. 1B further illustrates, at 101, 101B, a VCM production method and a related production unit adapted for cracking EDC in a single apparatus 100 comprising an arrangement (F1-F3) for extending residence time in reactive stages. The apparatus 100 of FIG. 1B thus comprises means for extraction of process fluid from the apparatus and for intake of additional fluid into the apparatus. Additional fluid may be any one of feed gas, a recycle gas, a make-up gas (a so-called replacement/supplement gas), a process fluid (transferred from a parallel apparatus for example), a dilution medium for any one of cooling/heating and the like. In some instances, any one of units F1, F2 and F3 within the arrangement may be configured as a heat exchanger, for example, to cool the process fluid. Cooling of the process within reactive stages may be used for further optimization of reaction yields.

Figure 2A:
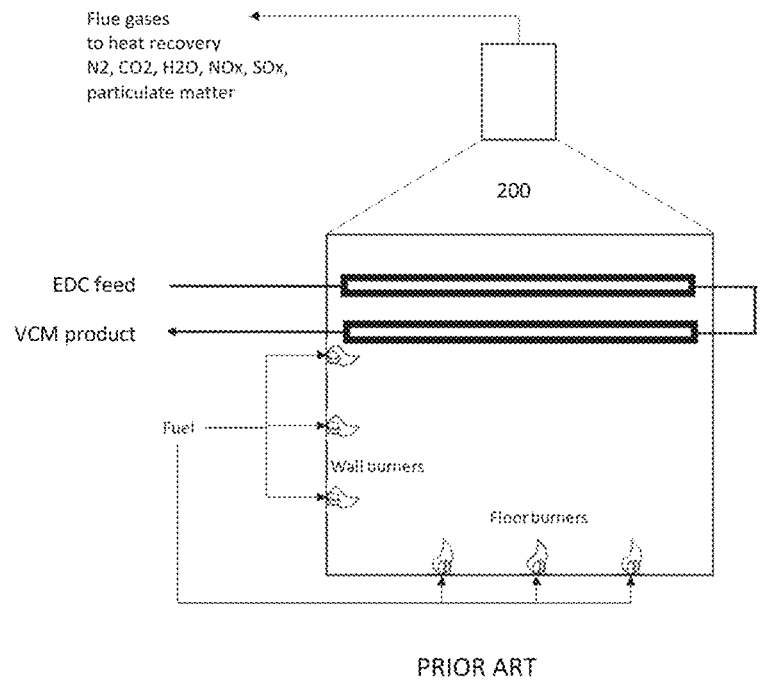
FIG. 2A schematically illustrates a conventional pyrolysis furnace.
Figure 2B:
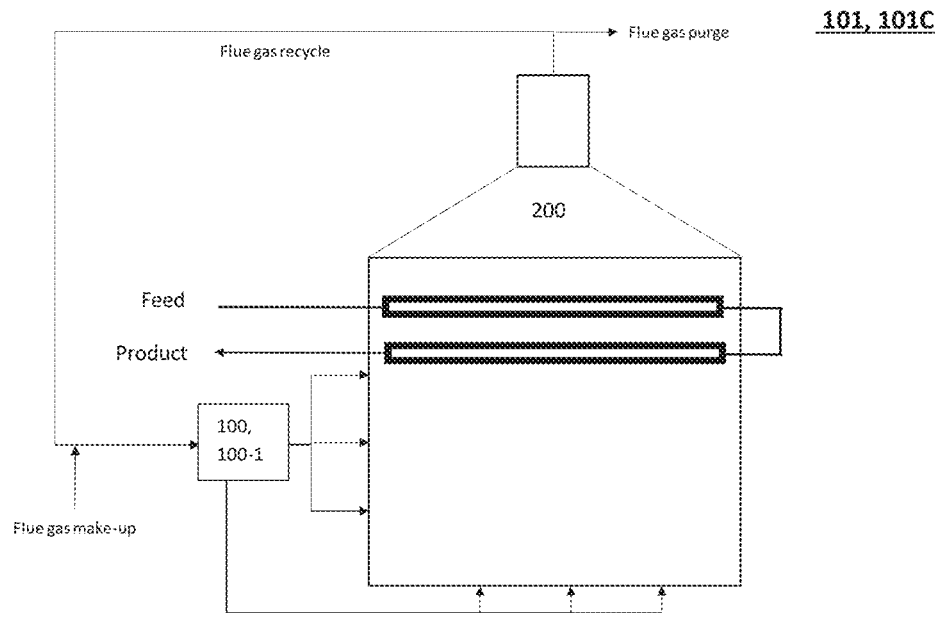
FIG. 2B schematically illustrates the VCM production method and related production unit according to the embodiment.

FIG. 2B illustrates, at 101, 101C, a VCM production method and a related production unit in accordance with another embodiment. Configuration of FIG. 2B involves using the rotary apparatus 100, 100-1 in indirect heating of the process fluid. In the method, cracking of EDC may be implemented in any pyrolysis furnace 200 suitable for that purpose, including any type of conventional EDC crackers. The furnace 200 may be configured as a cracking furnace suitable for thermal cracking of ethylene dichloride containing feed.

The amount of thermal energy required to heat the stream of the EDC-containing process fluid to temperature(s), at which cracking reactions occur, is produced and transferred to said EDC-containing process fluid using the rotary apparatus 100, 100-1, in which a heated fluidic medium is generated by virtue of adding the amount of thermal energy to the fluidic medium propagating therethrough. The heated fluidic medium produced in the apparatus 100, 100-1 may be inert gas, such as for example, air, nitrogen gas or steam, or any other matter suitable for the purposes of the invention. Heated fluidic medium is further used as a carrier to transfer thermal energy to the pyrolysis furnace 200 and to heat the stream of EDC-containing process fluid, flowing through said pyrolysis furnace, to the temperature(s), at which cracking reactions occur.

The heated fluidic medium used as a thermal energy carrier can be any species selected from the group consisting of: air, nitrogen gas, steam, flue gas(-es) exhausted from the pyrolysis furnace, and any combination thereof.

By using the apparatus 100, 100-1 for indirect heating of EDC-containing process fluids, performance of a conventional EDC cracking furnace can be improved. Operating principle of the conventional furnace, such as the one shown on FIG. 2A, is such that natural gas is fired inside a furnace firebox, and the flame and hot off-gases are heating reactor coils, inside which the reactants of EDC cracking are flowing. After delivering part of their heat for the reactants, the still hot off-gases are vented to the atmosphere. Typically, the temperature of the flue gases is above 120° C. to prevent condensation of water, which together with acidic species in the off-gas would create corrosive environment.

FIG. 2B shows how the apparatus 100, 100-1 can be used to replace fired heating in the furnaces. Fluidic medium, such as for example inert gas, is heated in the apparatus 100-1 to a predetermine temperature, and the heated fluidic medium is thus used to provide thermal energy to the EDC-containing process fluid flowing through the radiant coils of the furnace 200.

When hot effluent discharged from the apparatus 100, 100-1 is used as a heating medium, no carbon dioxide emissions is generated, since no incineration takes place. Flue gases generated during the cracking process in the furnace 200 can be at least partly recycled to be used as a heating medium in the apparatus 100, 100-1 (optionally mixed with inert gas, for example), within the unit 101 (101C, FIG. 2B). The amount of heat losses in flue gases discharged into the atmosphere can thus be markedly reduced.

Using the apparatus 100 as a heater in conjunction with conventional EDC pyrolysis furnaces 200 allows for reducing emissions and improving energy efficiency of the existing furnaces. Installation of the apparatus 100 into existing EDC cracker facilities can be realized with very low capital requirements, since a majority of process equipment does not need to be replaced. The existing furnaces 200 can be equipped with suitable piping arrangements around the reactor tube coils for example, to enable heat transfer from the fluid (e.g. inert gas) heated in the apparatus 100, 100-1 to the EDC-containing process fluid flowing through said coils.

An additional benefit achieved in indirect heating is improved temperature control. In conventional fired heaters the temperature of the flame is extremely high, in the range of 1800-2200° C. depending on fuel and air pre-heating. This raises temperature of furnace tubes, particularly in a lower, fired part of the furnace, and causes accelerated coking. With the apparatus 100, 100-1, temperature of the cracking furnace 200 can be maintained at lower levels. Additionally, more uniform heat distribution across the furnace can be achieved. This will markedly reduce coking rates and allow pushing the EDC cracking reaction above typical once-through conversion range of 60%, respectively, since coking will no longer be a limiting factor.

Figure 3:
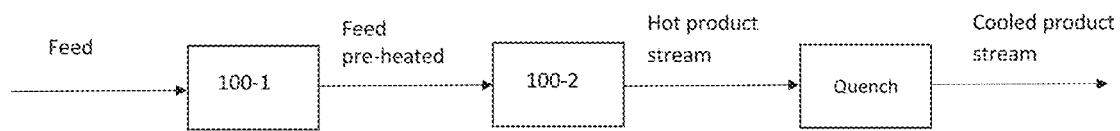
FIG. 3 schematically illustrates the VCM production method and related production unit according to the embodiment.

FIG. 3 illustrates, at 101, 101D, yet another embodiment of a VCM production method and a related production unit. In configuration of FIG. 3, at least two rotary apparatuses 100 are connecting into a system, in which a first apparatus 100-1 is rendered with a heater function to (pre)heat the EDC-containing process fluid (see description to FIG. 2B), whilst a second apparatus 100-2 arranged downstream of the first apparatus is rendered with a thermal cracker function. The apparatus 100-2 is configured to implement direct heating of the EDC-containing process fluid and it can be realized as the apparatus described with regard to any one of FIGS. 1A and 1B.

Configuration of FIG. 3 can be applied if there is a need to limit the reaction temperature (due to selectivity reasons, for example). In comparison to the apparatus 100 comprising (pre)heater stages and reactive stages in the same reactor (FIG. 1B), configuration of FIG. 3 involving at least two apparatuses 100-1, 100-2 enables separation of (pre)heating and reaction processes. In layout 101D, (pre)heating of process fluid and pyrolysis are performed in different apparatuses 100-1, 100-2, respectively, wherein the first apparatus in the sequence can be used for (pre)heating raw material(s), and the second apparatus in the sequence can be used for EDC cracking. Production unit 101D can further include means for extraction—and intake of fluids from—and to the apparatuses 100-1, 100-2 (as described with regard to FIG. 1B). Hence, any one of the apparatuses 100-1, 100-2 may include the arrangement (F1-F3) as described in relation to FIG. 1B.

For all configurations involving direct heating of the process fluid in the apparatus 100 (FIG. 1A, 1B and FIG. 3), the reactor unit 100, 100-2 can be designed such, as to improve selectivity. Achieving high reaction temperatures within the apparatus 100 in short time periods can be beneficial for overcoming low conversion rates.

The invention further pertains to a method for manufacturing polyvinylchloride (PVC) is provided by a process of polymerization of the vinyl chloride monomer obtained by embodiments of the VCM production method described hereinabove. Polymerization of VCM may be carried out in any facility suitable for that purpose.

In an aspect, the invention pertains to a vinyl chloride monomer (VCM) production unit for manufacturing VCM from ethylene dichloride (EDC) through thermal cracking.

In embodiment, the VCM production unit comprises at least one rotary apparatus 100, 100A, 100B, 100C configured to produce an amount of thermal energy required to heat a stream of EDC-containing process fluid to temperature(s), at which cracking reactions occur, and to transfer said amount of thermal energy to the EDC-containing process fluid. Said at least one rotary apparatus comprises: a rotor with a plurality of rotor blades arranged into at least one row over a circumference of a rotor hub mounted onto a rotor shaft; a plurality of stationary guide vanes arranged into row(s) upstream of the rotor blades; and a stationary diffuser arranged downstream of the rotor blades, wherein the rotor and the stationary vanes are enclosed in a duct formed in the rotary apparatus between at least one inlet and at least one outlet. The at least one rotary apparatus is thus configured to produce the amount of thermal energy by virtue of series of energy transformations occurring when a stream of fluidic medium propagated in the duct between the inlet(s) and outlet(s) successively passes through the stationary guide vanes, the rotor blades and the diffuser, respectively.

The VCM production unit can be configured with at least two rotary apparatuses connected in parallel and/or in series.

In embodiment, the at least one rotary apparatus within said VCM production unit is rendered with a thermal cracker function (rf. description to FIGS. 1A, 1B and 3).

In another embodiment, in said VCM production unit, the at least one rotary apparatus is rendered with a (pre)heater function configured to generate a heated fluidic medium by virtue of adding the amount of thermal energy to the fluidic medium propagating therethrough, and to transfer said amount of thermal energy to a pyrolysis furnace, such as for example a tubular cracking furnace, configured to carry out thermal cracking of EDC to yield VCM (rf. description to FIGS. 2B and 3).

The VCM production unit can be configured to comprise at least two rotary apparatuses connected into a system, in which a first apparatus is rendered with a preheater function to (pre)heat the EDC-containing process fluid, and a second apparatus arranged downstream of the first apparatus is rendered with a thermal cracker function (rf. description to FIG. 3).

In another aspect, the invention pertains to use of a rotary apparatus 100, 100A, 100B, 100C in production of vinyl chloride monomer (VCM) from ethylene dichloride (EDC) through thermal cracking. The apparatus thus comprises a rotor with a plurality of rotor blades arranged into at least one row over a circumference of a rotor hub mounted onto a rotor shaft; a plurality of stationary guide vanes arranged into row(s) upstream of the rotor blades; and a diffuser arranged downstream of the rotor blades, the rotor, the plurality of stationary guide vanes and the diffuser being enclosed in a duct formed in the rotary apparatus between at least one inlet and at least one outlet. The said use, an amount of thermal energy required to heat a stream of EDC-containing process fluid to temperature(s), at which cracking reactions occur, is produced in said rotary apparatus by virtue of series of energy transformations occurring when a stream of fluidic medium propagated in the duct between the inlet(s) and outlet(s) successively passes through the stationary guide vanes, the rotor blades and the diffuser, respectively, and further transferred to the EDC-containing process fluid.

Embodiments of the invention are further explained in the following non-limiting examples.

EXAMPLES

Direct Heating

Present examples involve configurations adapted for direct heating of EDC feed (FIGS. 1A, 1B, 3). Simulation data obtained in example cases 1-5 is summarized in Table 1. To simulate performance of a conventional EDC cracking furnace (comparative example case 1) and the rotary apparatus 100 (cases 2-5), AspenPlus V12.1 process simulation software (AspenTech) was used.

TABLE 1

Simulation data on example cases 1-5 for cracking EDC using the conventional EDC cracking furnace (comparative example case 1) and the rotary apparatus 100 (cases 2-5).

| | Example Case | Conversion | Selectivity to VCM | Selectivity to acetylene | Number of stages (100) | Maximum temperature Tmax (° C.) | Residence time |
|---|---|---|---|---|---|---|---|
| 1 | Conventional cracker (200) | 60% | 94.8% | 5.2% | 0 | 477 | 27 |
| 2 | Rotary apparatus (100) operating at temperatures within an average EDC cracking range | 60% | 94.8% | 5.2% | 4 | 520 | 19 |
| 3 | Rotary apparatus (100) operating at temperatures lower than the average EDC cracking range | 70% | 94.0% | 6.0% | 4 | 480 | 121 |
| 4 | Rotary apparatus (100) operating at temperatures higher than the average EDC cracking range | 70% | 91.4% | 8.6% | 5 | 600 | 3 |
| 5 | Rotary apparatus (100) configured to implement instant heating | 60% | 93.8% | 6.2% | 4 | 726 | 5 |

Although pyrolysis involves hundreds of reactions with molecular compounds and radicals, a simplified computational model was adopted for simulating thermal cracking kinetics mechanism (Reaction 1) taken that pyrolysis reactions occurring in the EDC cracker involve the following components: EDC, VCM, hydrogen chloride (HCl), and a byproduct represented by acetylene ($C_2H_2$). Hence, in addition to simulating kinetics of a main reaction (Reaction 2a), kinetics of side reactions involving formation of acetylene as a model byproduct contributing to formation of coke, were also simulated (Reaction 2b).

EDC→VCM→byproduct     Reaction 1.

EDC→VCM+HCL     Reaction 2a.

VCM→ACETYLENE+HCL     Reaction 2b.

Case 1 is a comparative example, where EDC cracking process was simulated in a conventional, tube-type furnace.

For Case 1, data on the furnace system and its simplified EDC cracking kinetics mechanism as discussed in Li et al. (2013) [1] were used. Based on the mentioned literature source, simulated furnace had two rows of reactor coils (including 20 straight tubes and 19 bends per row) having inlet tube diameter of about 0.1 m and had EDC feed rate of 42 t/h with an inlet temperature of about 260° C. and pressure of about 2400 kPa. With these parameters, residence time the process fluid spends to pass through coils is 26-27 s. Adiabatic volume (last part of the reactor before the quench) was assumed equal in all cases: Residence time in the adiabatic volume was about 0.06 s. Temperature profile throughout the reactor defines the extent of reactions. Temperature profile and mass fraction profile for comparative Case 1 are shown on FIGS. 5A and 5B, respectively.

Figure 5A:
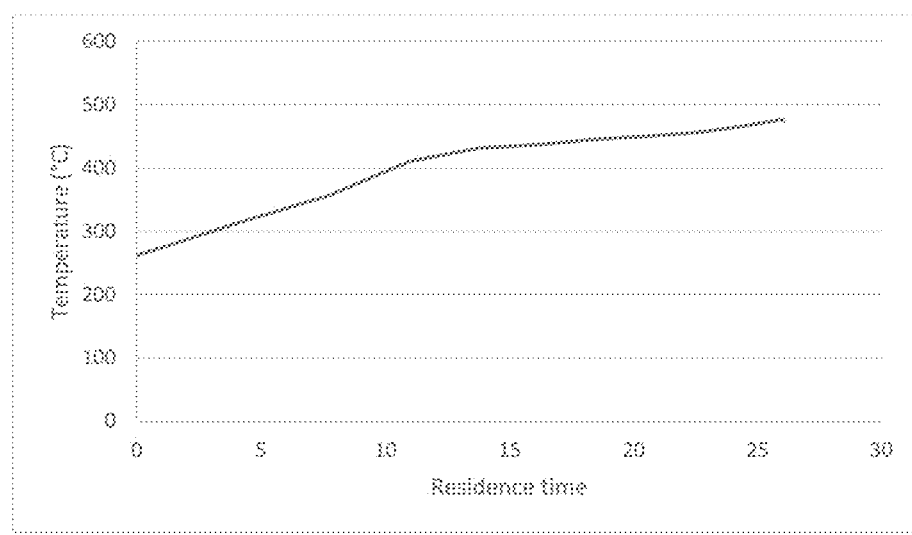
FIGS. 5A-9B show temperature profiles and mass fraction profiles obtained in Example Cases 1-5.
Figure 5B:
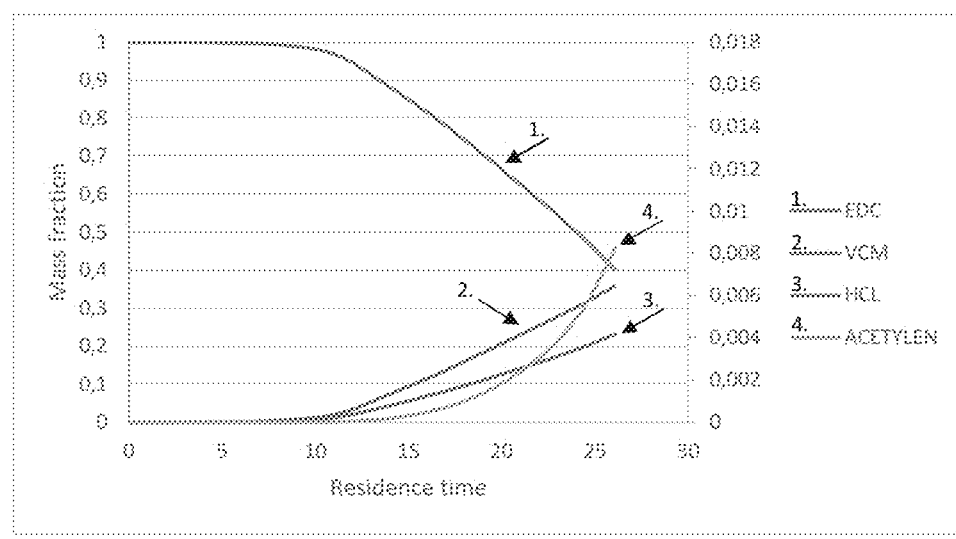

Temperature profile as shown on FIG. 5A is typical for a conventional EDC cracker. Process temperature rises steadily from 260° C. (feed gas temperature) until about 400° C., where endothermic reactions start to take place; from which point on the rate of temperature rise decreases and evens out. Reaction rate is low in the first part of the reactor (rf. FIG. 5B). As the EDC-containing process fluid propagates towards to the reactor outlet, the rate of chemical reactions increases to such an extent that immediate quench is needed.

Example cases 2-5 were simulated for the apparatus 100, 100A as illustrated on FIG. 4A.

Figure 6A:
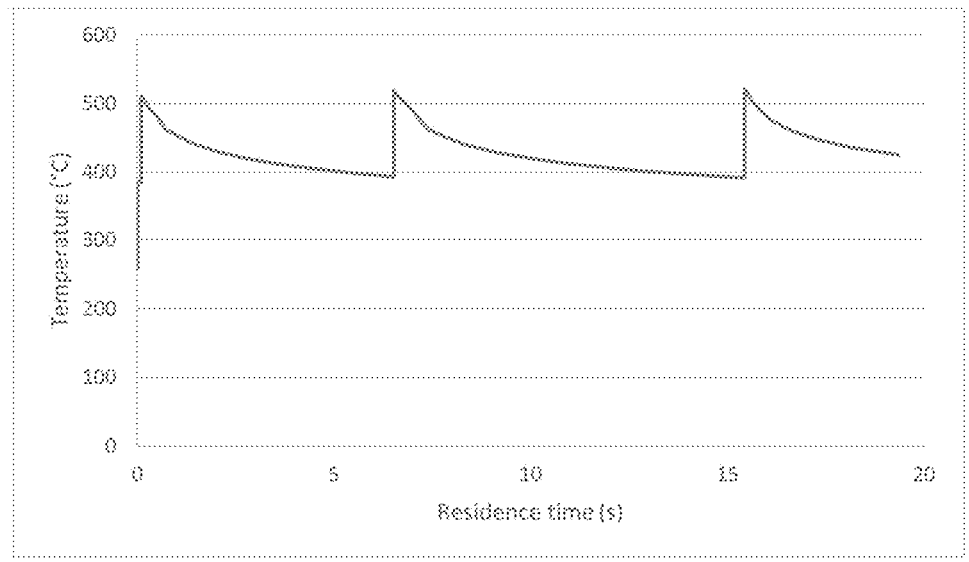
Figure 6B:
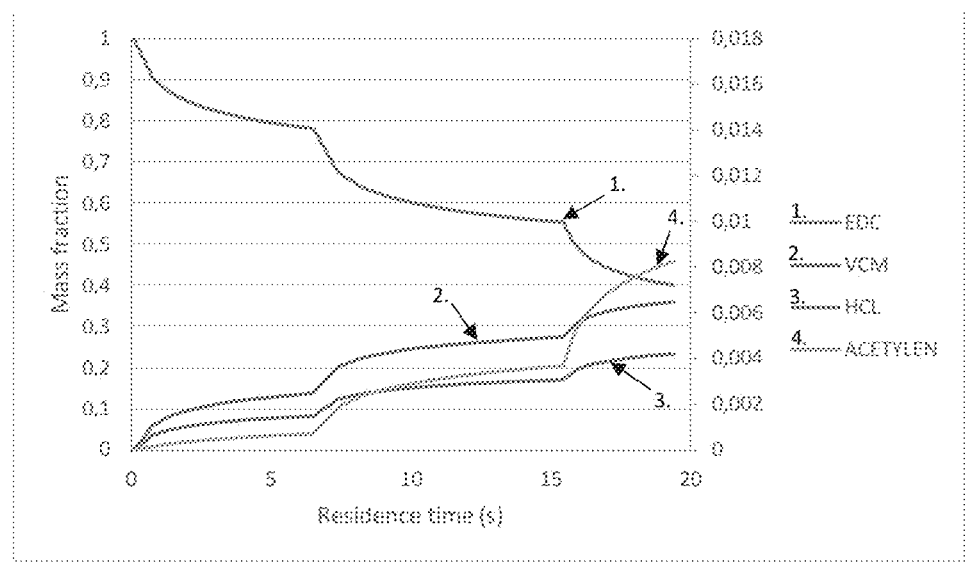
Figure 7A:
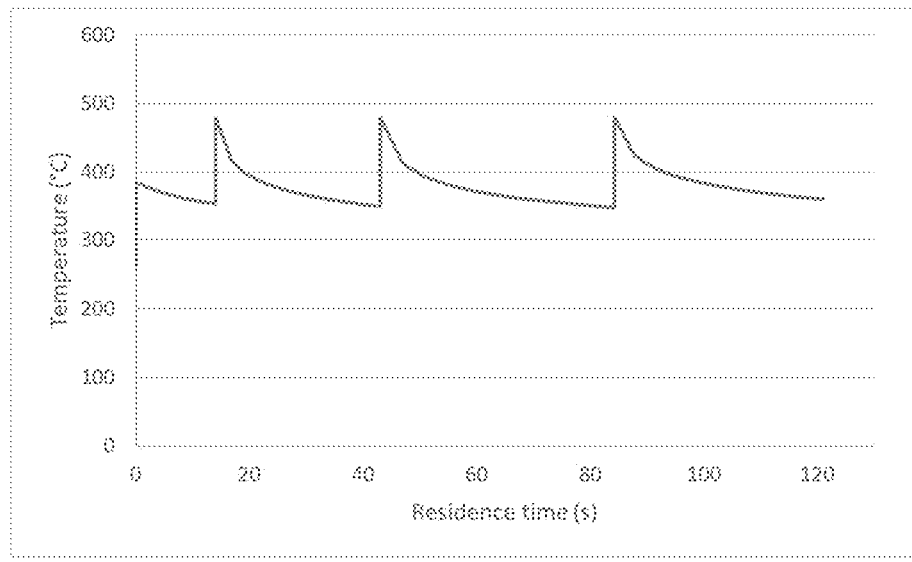
Figure 7B:
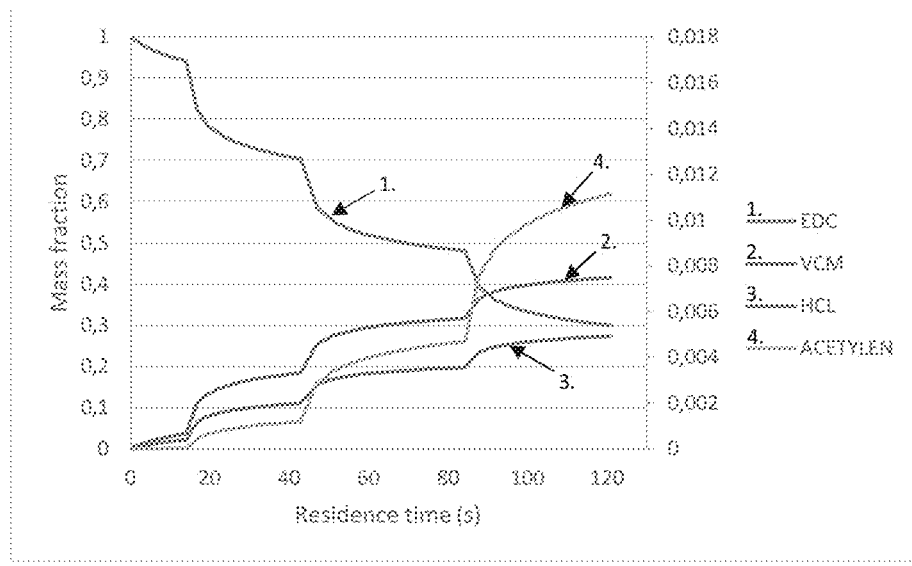
Figure 8A:
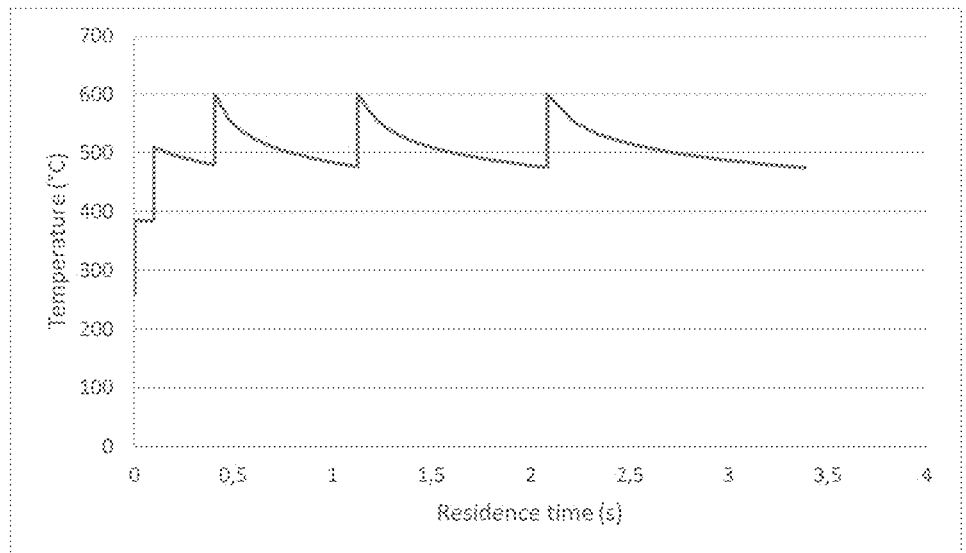
Figure 8B:
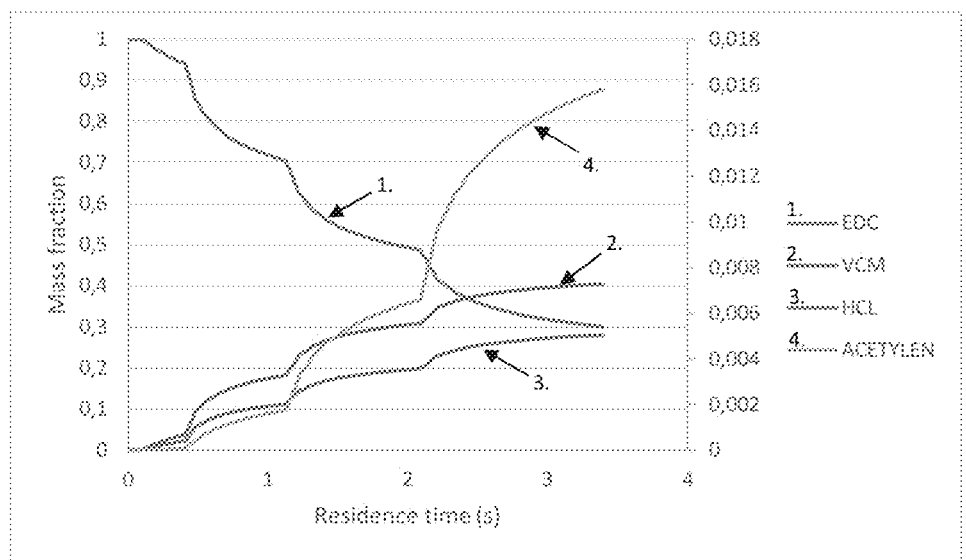

Case 2 was modelled in order to show that the apparatus 100 operating at temperatures within an average EDC cracking range ($T_{max}$ 520° C.) can successfully replace a conventional EDC cracker. Temperature profile and mass fraction profile for Case 2 are presented on FIGS. 6A and 6B, respectively.

Case 2 was simulated with four (4) working stages realized, in configuration 100A, as four stator-rotor-diffuser sequences 2, 3, 4, wherein each stage heats the EDC-containing gaseous process fluid by approximately 120° C. (delta T ($\Delta T$)=120° C.). First two stages were assumed to situate at the beginning of the reactor and represent so called (pre)heating stages. These stages may locate either in the apparatus 100 (100A) configured as a thermal cracker (FIGS. 1A, 1B) or, alternatively, these stages may locate in the apparatus 100-1 configured as a (pre)heater. In present simulation, last two stages were assumed to represent so called reactive stages.

In the simulation involving a single reactor unit 100 (rf. FIGS. 1A, 1B), within 1-5 milliseconds, the reactor is heated to about 510° C. (during first two preheating stages). At this point, with decomposition of EDC, the temperature of gas flow decreases due to endothermic reactions between the stages (the EDC-containing process fluid passes through the vaneless portion of the duct 7, 7A). Residence time of about 6 seconds is allowed until the process fluid enters the third working stage to be re-heated to about 520° C. Thereafter, process temperature is allowed to drop again, and the process is further re-heated to about 520° C. in a final, fourth working stage. Due to endothermic reactions occurring in the process fluid, at the reactor exit the process fluid may have a lower temperature as compared to conventional reactor furnaces (compare graphs FIGS. 5A and 6A). In various configurations (100A, 100B or 100C), the apparatus 100 can be configured with the adiabatic volume within the reactor (part of the duct 7 between the last working stage and the reactor exit) optimized such as to meet the requirements of the process. Optimization may be performed by modifying (e.g. reducing or expanding) a three-dimensional spread within the apparatus accommodating the adiabatic volume.

The rate of acetylene generation is clearly lower in the apparatus 100 (at the exit thereof) than in conventional cracker. This results in reduced coke formation in the reactive areas of the apparatus 100 and at its exit.

Overall, residence time required for cracking reactions to occur is shorter for the apparatus 100, because higher reaction temperatures ($T_{max}$) can be achieved.

Cases 3 and 4 were modelled for the apparatus 100 operating at temperatures deviating from the average EDC cracking temperature (taken as apprx. 520° C., see Case 2). Case 3 was designed for the operating temperature lower than the average EDC cracking temperature, whilst Case 4—for the operating temperature higher than average EDC cracking temperature, respectively. On the other hand, as compared to the conventional cracker of Case 1, Case 3 was modelled for the apparatus 100 operating at a maximum temperature ($T_{max}$ 480° C.) similar to that of the conventional EDC cracking furnace; whilst Case 4 was modelled for the apparatus 100 operating at a maximum temperature ($T_{max}$ 600° C.) higher than that of the conventional EDC cracking furnace. Heat input per stage was same as before: $\Delta T$=120° C. Nevertheless, the delta T parameter can be optimized on a case-to-case basis. Temperature profiles and mass fraction profiles for Cases 3 and 4 are presented on FIGS. 7A, 8A and 7B, 8B, respectively.

Cases 3 and 4 both run to higher conversion rates than the conventional cracker (Case 1). Lowering the operating temperature (Case 3) extends residences times the process fluid spends in the reactor beyond those typically required for pyrolysis reactions to occur and so it appears beneficial to conduct the process of Case 3 in the apparatus 100 configured as suggested by FIG. 1B. Increasing the operating temperature (Case 4) reduces the required residence times to about one tenth of that in the conventional cracker.

Another noticeable difference between Cases 3 and 4 is selectivity. Simulated kinetics suggests that lower temperatures and high residence times (Case 3) improve process selectivity, as compared to the conventional cracking furnace of Case 1. This opens a possibility to run the cracking process to higher conversion rates, along with reducing coke formation.

Most of byproducts, such as acetylene, is produced at the end of the cracking process. In the kinetics model utilized herewith, a reaction of acetylene formation is driven by an increase in VCM concentration. High reaction temperatures also promote generation of acetylene. A combination of high reaction temperatures and high conversion rate is therefore an unwanted situation.

Figure 9A:
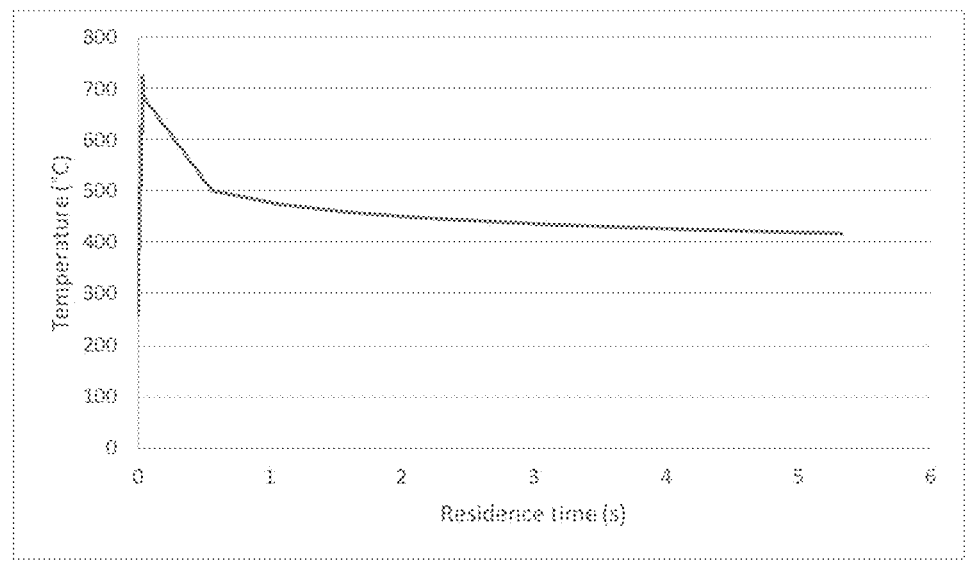
Figure 9B:
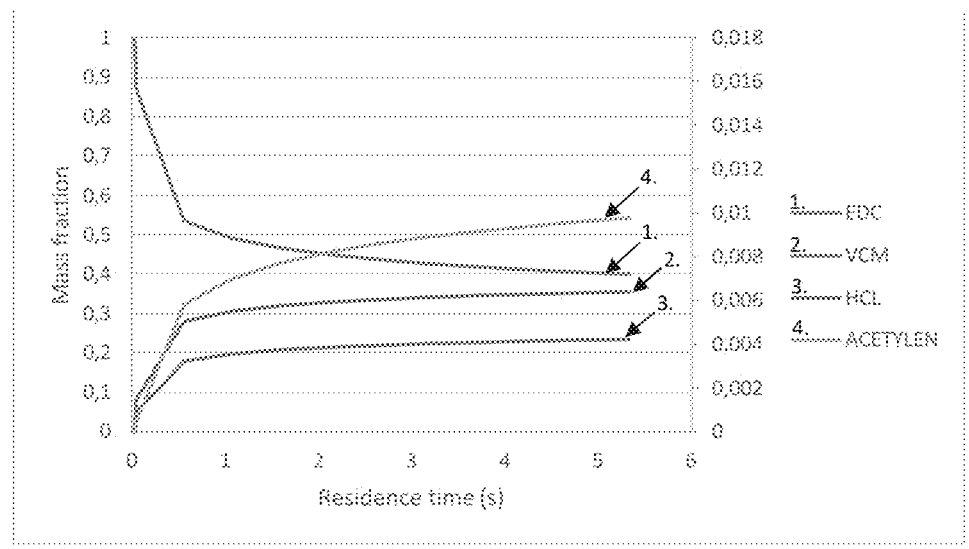

Case 5 aims at sorting out, whether rapid heating to high temperatures (reactions temperature at which pyrolysis of EDC occurs) in the beginning of the reactor 100, has a positive effect on selectivity. Case 5 was simulated with four (4) working stages, where each stage is defined as a stator-rotor-diffuser sequence 2, 3, 4. On the contrary to Case 2, in present Case 5 all four stages situate in the first part of the reactor directly at the reactor inlet in order to instantly heat the feed gas to unusually high temperatures of almost 730° C. Temperature profile and mass fraction profile for Case 5 are presented on FIGS. 9A and 9B, respectively.

In Case 5, the reaction starts with EDC decomposition at a high rate. Within apprx. 40 milliseconds about 13% conversion is achieved; and about 50% conversion is reached within one second. The process fluid reaches the adiabatic volume at the end of the reactor during a time period of only 5.3 seconds (residence time=5.3 s). During that time 60% EDC conversion rate is achieved. However, despite our initial assumption that formation of acetylene could be controlled by such instant heating step (due to decrease in process fluid temperatures accompanying the rise in VCM concentration), the system has demonstrated lower selectivity to VCM and higher acetylene concentrations.

Heat Losses

According to the literature sources (rf. for example Li et al. [1]), conventional cracking uses approximately 1000 kg/h of fuel gas. From the heat of combustion, one can estimate that the total energy output of the furnace is 13 MW. Simulation estimates that the conventional EDC cracker requires energy of about 8.3 MW to heat the process fluid at which cracking reactions occur, which leads to flue gas losses of about 4.7 MW. According to the above referenced document, the temperature of flue gas (that accounts for the most of heat losses) at the furnace outlet is 900 K and calculating back to near atmospheric conditions using an estimated heat capacity and a decrease in flue gas temperature results in essentially the same energy loss value. Therefore, about 36% of the heat input to a conventional EDC cracker is lost.

On the other hand, when the rotary apparatus 100 is used for direct heating of feedstocks (rf. FIGS. 1A, 1B, 3), heat losses may be negligible, and these heat losses arise mainly due to the motor output and drive efficiency. For example, efficiency of the rotary apparatus 100 driven with electric motor has been estimated as about 94%. Therefore, its energy losses are about six (6) times smaller than those occurring in the conventional EDC cracker. Heat inputs and losses for Cases 1-5 are presented in Table 2.

TABLE 2

Heat inputs and losses for Example Cases 1-5.

| Case number | Total heat input (MW) | Heat utilized in reactor (MW) | Heat losses (MW) |
|---|---|---|---|
| 1 | 13 | 8.3 | 4.7 |
| 2 | 8.1 | 7.6 | 0.5 |
| 3 | 8.1 | 7.6 | 0.5 |
| 4 | 10 | 9.4 | 0.6 |
| 5 | 8.1 | 7.6 | 0.5 |

Higher heat input in Case 4 is explained by a provision of an additional working stage. Additional heat that has not been consumed, in Case 4, by the endothermic reaction to provide yet increased conversion rate becomes available in the product gas for further integration (through recycling) to the feed heating. Differences in values designating heat utilized in the reactor (MW) pertain to the differences in outlet temperatures and conversion rates.

Indirect Heating

Examples below involve configurations adapted for indirect heating of EDC feed in the cracking furnace 200, where the apparatus 100, 100-1 is rendered with a (pre)heater function (FIG. 2B). With the indirect heating using the rotary apparatus 100, 100-1 the cracking reactions and thermal decomposition temperature profiles respectively could proceed as suggested by the Case 1 with a difference that coil tube temperatures could be decreased, and the coke formation reduced, accordingly. Local temperature differences within the cracker furnace would also be smaller.

A major benefit of the indirect heating approach is energy efficiency. Because no flue gas is produced, a heating medium (viz. a heat transfer medium) can be recycled back to the rotary apparatus for reheating. Assuming a rather high purge rate of 5%, the heat losses resulting from flue gas are 5% of the conventional EDC cracker at 0.23 MW. An additional loss arises from the motor output and drive efficiency. With the heat consumption in the cracking furnace (200) being about 8.3 MW and with about 0.23 MW reserved for flue gas losses, the rotary apparatus 100, 100-1 has to produce about 9.1 MW of heat. The heat loss can be estimated at 0.54 MW. Hence, the total heat loss in the indirect heating approach is about 0.79 MW and this heat loss is slightly over a tenth part of losses observed in the conventional EDC cracker.

It is clear to a person skilled in the art that with the advancement of technology the basic ideas of the present invention may be implemented and combined in various ways. The invention and its embodiments are thus not limited to the examples described herein above, instead they may generally vary within the scope of the appended claims.

REFERENCES

[1] Chaochun Li, Guihua Hu, Weimin Zhong, Hui Cheng, Wenli Du, and Feng Qian, Comprehensive Simulation and Optimization of an Ethylene Dichloride Cracker Based on the One-Dimensional Lobo-Evans Method and Computational Fluid Dynamics, Ind. Eng. Chem. Res. 2013, 52, 2, 645-657.

The invention claimed is:

1. A method for manufacturing vinyl chloride monomer (VCM), the method comprises: subjecting ethylene dichloride (EDC) to thermal cracking to yield a VCM-containing gaseous product,
   wherein thermal energy required to heat a stream of EDC-containing process fluid to temperature(s), at which cracking reactions occur, is produced and transferred to said EDC-containing process fluid using a rotary apparatus comprising:
       a rotor with a plurality of rotor blades arranged into at least one row over a circumference of a rotor hub mounted onto a rotor shaft;
       a plurality of stationary guide vanes arranged into row(s) upstream of the rotor blades; and
       a stationary diffuser arranged downstream of the rotor blades,
       wherein the rotor, the stationary guide vanes and the diffuser are enclosed in a duct formed in the rotary apparatus between at least one inlet and at least one outlet,
   wherein, said thermal energy is produced, in the rotary apparatus, by virtue of series of energy transformations occurring when a stream of fluidic medium propagated in the duct between the inlet(s) and outlet(s) successively passes through the stationary guide vanes, the rotor blades and the diffuser, respectively.

2. The method of claim 1, comprising subjecting EDC to thermal cracking in the rotary apparatus, wherein cracking reactions are initiated in the EDC-containing process fluid propagating through the rotary apparatus by virtue of adding thermal energy in an amount required for the cracking reactions to occur directly to the stream of EDC-containing process fluid.

3. The method of claim 1, comprising subjecting EDC to thermal cracking in a pyrolysis furnace suitable for that purpose, the method further comprising:
   in the rotary apparatus, generating a heated fluidic medium by virtue of adding thermal energy to the fluidic medium propagating therethrough, and
   using said fluidic medium as a carrier to transfer thermal energy to the pyrolysis furnace and to heat the stream of EDC-containing process fluid, flowing through said pyrolysis furnace, to the temperature(s), at which cracking reactions occur.

4. The method of claim 3, wherein the heated fluidic medium used as the thermal energy carrier is any one of air, nitrogen gas, steam, flue gas(-es) exhausted from the pyrolysis furnace, and any combination thereof.

5. The method of claim 3, wherein the pyrolysis furnace is any cracking furnace suitable for thermal cracking of ethylene dichloride containing feed.

6. The method of claim 1, comprising connecting at least two rotary apparatuses into a system, in which a first apparatus is rendered with a preheater function to (pre)heat the EDC-containing process fluid, and a second apparatus arranged downstream of the first apparatus is rendered with a thermal cracker function.

7. The method of claim 1, further comprising conducting input energy into the at least one rotary apparatus, wherein, by adjusting the amount of said input energy conducted into the at least one rotary apparatus, the amount of thermal energy, which is added to the stream of fluidic medium propagated through the rotary apparatus is regulated.

8. The method of claim 7, wherein the input energy is electrical energy.

9. The method of claim 8, wherein the amount of electrical energy conducted as the input energy into the at least one rotary apparatus is within a range of about 5 percent to 100 percent.

10. The method of claim 8, wherein electrical energy conducted as the input energy into the at least one rotary apparatus is obtainable from a source of renewable energy or a combination of different sources of energy, optionally, renewable energy.

11. The method of claim 1, comprising adjusting velocity and/or pressure of the stream of fluidic medium propagating through the rotary apparatus to produce conditions, at which kinetic energy is added to the stream of fluidic medium by rotating blades of the rotor in an amount sufficient to raise the temperature of the fluidic medium to a predetermined value when said stream of fluidic medium exits the at least one row of rotor blades at a supersonic speed and passes through the stationary diffuser, where stream decelerates and dissipates kinetic energy into an internal energy of the fluidic medium, whereupon thermal energy is added to the stream of fluidic medium.

12. The method of claim 11, in which thermal energy added to the stream of fluidic medium propagating through the rotary apparatus is produced by virtue of generation of a system of shock waves during successive propagation of said stream of fluidic medium through the rows of stationary guide vanes, the row of rotor blades and the stationary diffuser, respectively, in a controlled manner.

13. A method for manufacturing polyvinylchloride (PVC) by polymerization of the VCM obtained by the method of claim 1.

14. A method of use of a rotary apparatus comprising a rotor with a plurality of rotor blades arranged into at least one row over a circumference of a rotor hub mounted onto a rotor shaft; a plurality of stationary guide vanes arranged into row(s) upstream of the rotor blades; and a diffuser arranged downstream of the rotor blades, the rotor, the plurality of stationary guide vanes and the diffuser being enclosed in a duct formed in the rotary apparatus between at least one inlet and at least one outlet, in production of vinyl chloride monomer (VCM) from ethylene dichloride (EDC) through thermal cracking, wherein thermal energy required to heat a stream of EDC-containing process fluid to temperature(s), at which cracking reactions occur, is produced in said rotary apparatus by virtue of series of energy transformations occurring when a stream of fluidic medium propagated in the duct between the inlet(s) and outlet(s) successively passes through the stationary guide vanes, the rotor blades and the diffuser, respectively, and further transferred to the EDC-containing process fluid.

15. The method of claim 14, wherein the rotary apparatus is rendered with a thermal cracker function.

16. The method of claim 14, wherein the rotary apparatus is rendered with a preheater function configured to generate a heated fluidic medium by virtue of adding the amount of thermal energy to the fluidic medium propagating therethrough, and to transfer said amount of thermal energy to a pyrolysis furnace configured to carry out thermal cracking of EDC to yield VCM.

17. The method of claim 16, wherein the pyrolysis furnace is a tubular cracking furnace.

18. The method of claim 14, wherein the rotary apparatus is electrically driven.

19. The method of claim 14, wherein the at least one rotary apparatus is configured to implement a fluidic flow, between the inlet and the exit, along a flow path established in accordance with any one of: an essentially helical trajectory formed within an essentially toroidal-shaped casing; an essentially helical trajectory formed within an essentially tubular casing, an essentially radial trajectory, and along the flow path established by virtue of the stream of fluidic medium in the form of two spirals rolled up into vortex rings of right and left directions.

* * * * *